United States Patent [19]

Donachy et al.

[11] Patent Number: 5,284,936

[45] Date of Patent: * Feb. 8, 1994

[54] POLYAMINO ACID SUPERABSORBENTS

[75] Inventors: Julie Donachy; C. Steven Sikes, both of Mobile, Ala.

[73] Assignee: University of South Alabama, Mobile, Ala.

[*] Notice: The portion of the term of this patent subsequent to Sep. 21, 2010 has been disclaimed.

[21] Appl. No.: 870,241

[22] Filed: Apr. 17, 1992

Related U.S. Application Data

[63] Continuation-in-part of Ser. No. 677,333, Mar. 29, 1991.

[51] Int. Cl.$^5$ .............. A61F 13/15; B01J 20/26; C07K 15/00; C08L 77/04
[52] U.S. Cl. .............. 530/350; 502/402; 502/403; 525/54.1; 525/432; 528/310; 528/321; 528/328; 530/300; 530/352; 604/365; 604/372
[58] Field of Search .............. 530/300, 350, 352; 502/402, 403; 604/365, 372; 514/2, 7; 525/54.11, 54.1, 432; 528/310, 321, 328

[56] References Cited

U.S. PATENT DOCUMENTS

| | | | |
|---|---|---|---|
| Re. 32,649 | 4/1988 | Brandt et al. | 604/368 |
| 3,474,083 | 10/1969 | Shiga et al. | 528/328 |
| 3,948,863 | 4/1976 | Akamatsu et al. | 606/231 |
| 4,534,881 | 8/1985 | Sikes et al. | 210/698 |
| 4,585,560 | 4/1986 | Sikes et al. | 210/698 |
| 4,587,021 | 5/1986 | Wheeler et al. | 210/698 |
| 4,590,260 | 5/1986 | Harada et al. | 528/310 |
| 4,654,039 | 3/1987 | Brandt et al. | 604/368 |
| 4,703,067 | 10/1987 | Mikita et al. | 521/63 |
| 4,771,089 | 9/1988 | Ofstead | 524/41 |
| 4,777,231 | 10/1988 | Bailey et al. | 526/203 |
| 4,833,222 | 5/1989 | Siddal et al. | 526/200 |
| 4,866,161 | 9/1989 | Sikes et al. | 530/324 |
| 4,868,287 | 9/1989 | Sikes et al. | 530/324 |
| 4,892,733 | 1/1990 | Bichon et al. | 528/328 |
| 4,996,292 | 2/1991 | Fox et al. | 528/328 |
| 5,051,401 | 9/1991 | Sikes | 514/7 |
| 5,204,099 | 4/1993 | Barbier et al. | 530/328 |

OTHER PUBLICATIONS

Overell et al., "Polymers of Some Basic and Acidic α-Amino Acids", *J. Chem. Soc.*, 1955, pp. 232–236.

Fox et al., *J. Am. Chem. Soc.*, vol. 82, pp. 3745–3751 (1959).

Fox et al., *Science*, vol. 128, p. 1214 (1958).

*Primary Examiner*—Jeffrey E. Russel
*Attorney, Agent, or Firm*—Oblon, Spivak, McClelland, Maier & Neustadt

[57] ABSTRACT

Substantially water-insoluble, crosslinked polypeptides containing 15 to 85 mole % of amino acid residues such as glutamic acid, aspartic acid, phosphoserine, phosphohomoserine, phosphotyrosine, phosphothreonine, phosphoasparagine, or phosphoglutamine, and 15 to 85 mole % of amino acid residues such as lysine, arginine, asparagine, glutamine, serine or tyrosine, in which the degree of crosslinking is sufficient to result in a substantially water-insoluble polypeptide with the ability to absorb a 1 wt. % aqueous NaCl solution in an amount of at least 20 times the weight of the polypeptide, are useful as superabsorbents in devices such as diapers, etc. Mild alkaline hydrolysis of the crosslinked polypeptides increases their superabsorbency by two to three fold.

3 Claims, No Drawings

POLYAMINO ACID SUPERABSORBENTS

This application is a continuation-in-part of U.S. application Ser. No. 07/677,333, filed Mar. 29, 1991, which is incorporated by reference.

BACKGROUND OF THE INVENTION

1. Field of the Invention

The present invention relates to new polypeptides that have the capability of absorbing large amounts of water and aqueous solutions, in particular physiological saline solutions, and methods for preparing such polypeptides. These polymers are useful in a variety of applications including but not limited to sanitary goods, hygienic goods, water retaining agents, dehydrating agents, and control release agents for various chemicals.

2. Discussion of the Background

In general, superabsorbent polymers possess a structure in which the water-soluble polymer has been made insoluble by some process, typically by means of a cross-linking agent, resulting in polymers that have the power to absorb at least 20 times their weight in pure water. Water absorbing resins currently in use include hydrolysis products of starch-acrylonitrile graft polymers, carboxymethylcellulose, polycarboxylic acids, acrylamides, non-cross-linked polymer blends, cross-linked polyacrylate products and other resins such as polyvinyl alcohols (Mikita et al, U.S. Pat. No. 4,703,067; Ofstead, R. F., U.S. Pat. No. 4,771,089; and Siddall, J. H. et al, U.S. Pat. No. 4,833,224). Brandt et al, U.S. Pat. No. Re. 32,649 also disclose hydrogel-forming polymer compositions based on polymerized unsaturated polymerizable acid group-containing monomers and a cross-linking agent. Superabsorbent polymers are polyanionic in nature and it is the hydration of these charged groups that leads to the absorbent characteristics (Masuda, F., "Super absorbent polymers—characteristics and trends in development of applications," *Chem. Econ. Enginer. Rev.*, vol. 15, pp. 19–23 (1983)).

One problem with such resins is that the absorptive capacity is greatly reduced in the presence of physiological salines. This is an important aspect, in view of the uses of these polymers in diapers and personal hygiene applications. Additional drawbacks of these resins include cumbersome processes of syntheses in some cases and low heat resistance and rapid decay in other instances.

Mixtures of α-amino acids can be thermally polymerized into proteinoids (Fox and Harada, *Science*, vol. 128, p. 1214 (1958) and *J. Am. Chem. Soc.*, vol. 82, pp. 3745–3751 (1959)) at temperatures above 150° C. The syntheses require the presence of excess dicarboxylic amino acids for unknown reasons. However, the advantage of excess dicarboxylic amino acid is lost above 210° C., with thermal decomposition of the amino acids. High reproducibility in copolymerization of amino acids has been reported (Fox and Windsor, *International Journal of Quantum Chemistry: Quantum Biology*, vol. 11, pp. 103–108 (1984)).

However, there are no reports of polyanionic polymers that have specific amino acids incorporated into them that effectively cross-link the polymer during the thermal polymerization or provide sites for post-synthesis chemical crosslinking, or methods for preparing such polymers. In particular, there are no reports of conditions that result in the formation of an insoluble product, capable of absorbing large amounts of water.

Thus, there remains a need for new molecules that function as superabsorbents and a method of preparing such compounds.

SUMMARY OF THE INVENTION

Accordingly, it is an object of the present invention to provide new materials which function as superabsorbents.

It is another object of the present invention to provide a method for the synthesis of such compounds.

It is another object of the present invention to provide materials that function as superabsorbents in personal hygiene goods.

It is another object of the present invention to provide materials that function as water retaining agents.

It is another object of the present invention to provide materials that function as dehydrating agents.

It is another object of the present invention to prepare superabsorbent compounds that contain low levels of extractable compounds.

These and other objects of the present invention, which will become apparent during the course of the following detailed description have been achieved by providing new polypeptides which are substantially water-insoluble and crosslinked and consist essentially of 15 to 85 mole % of X residues and 15 to 85 mole % of Y residues, in which X is selected from the group consisting of aspartic acid, glutamic acid, sulfur and phosphor-based derivatives including but not limited to phosphoserine, phosphohomoserine, phosphotyrosine, phosphothreonine, phosphoasparagine, and phosphoglutamine, Y is selected from the group consisting of lysine, arginine, asparagine, glutamine, serine, tyrosine, other amino acids which provide a side chain that can function as a cross-linking site, and mixtures thereof, and in which the degree of crosslinking of the polypeptide is sufficient to result in an insoluble peptide and an ability to absorb saline in an amount at least 20 times the weight of the polypeptide and the crosslinking is between groups on the same or different polypeptide chains.

DESCRIPTION OF THE PREFERRED EMBODIMENTS

Thus, the present invention identifies and describes new polypeptide molecules which are insoluble and can absorb large quantities of water, biological fluids, or physiological saline solutions. These materials preferably have a polyanionic backbone such as polyglutamic or polyaspartic acid. The remainder of the molecule is composed of, e.g., lysine residues or other amino acids which provide side chain cross-linking sites.

In a preferred embodiment, X is aspartate or glutamate, particularly preferably aspartate, and most preferably polyaspartate of 10 to 60 amino acid residues; Y is lysine, arginine, asparagine, glutamine, serine or threonine, particularly preferably lysine. When X is aspartic acid, the preferred amino acid composition is from 15 to 25 mole % lysine, 75 to 85 mole % aspartic acid, preferably 17 to 20 mole % lysine, 80 to 83 mole % aspartic acid.

In another preferred embodiment, X is glutamate, and Y is lysine, arginine, asparagine, glutamine, serine or threonine, particularly preferably lysine. When X is glutamate, the preferred amino acid composition of this peptide is 50 to 80 mole % lysine, 20 to 50 mole % glutamic acid, most preferably 60 to 70 mole % lysine, 30 to 40 mole % glutamic acid.

The present polypeptides are crosslinked and water insoluble. The degree of crosslinking is sufficient to render the molecule insoluble and having the ability to absorb saline in an amount of at least 20 times, preferably at least 30 times, most preferably at least 40 times, the weight of the polypeptide. The crosslinking is between the amino groups or hydroxyl groups of Y and the anionic groups of X. It is to be understood that the crosslinking may occur between groups on Y and X residues contained within the same polymeric backbone or chain or between groups on X and Y residues contained within the backbone of different polymer chains.

The relative absorbency and degree of crosslinking may be easily controlled by proper selection of the time and temperature parameters utilized in the synthesis of the polypeptide. This aspect of the invention will be described more fully below.

As noted above, the present polypeptides are useful for the absorption of water or biological fluids and may be used in devices such as diapers, sanitary napkins, etc. In addition, the present polypeptides may be used for the controlled release of a chemical.

The present superabsorbent polypeptides may be conveniently prepared by a one-step process. The amino acids to be incorporated in the polypeptide are placed in a flask in amounts which correspond to the ratios of the amino acid residues in the polypeptides, and the mixture is heated to a temperature of 190° to 250° C. Alternatively, a prepolymerized polypeptide, such as, e.g., polyaspartic acid, may be substituted, in whole or in part, for one or more of the amino acids. An advantage of the present process is that no solvent is required. When incorporating Lys as Y, the use of Lys-HCl may be advantageous. In particular, when the pH of the reaction mixture is neutral or above, it may be necessary to add Lys in the form of Lys-HCl to the reaction mixture.

As noted above, the absorbency and the degree of crosslinking in the final product can be controlled by varying the time and temperature of the heating step. Although for any particular combination of starting materials the optimum temperature and time may vary, good results are generally achieved when the temperature is 190° to 250° C. and the heating is carried out for a time of 4 to 36 hours. In particular, for polypeptides in which X is Asp and Y is Lys, the temperature is preferably 210° to 230° C., most preferably about 220° C., and the time is preferably 12 to 24 hours, most preferably about 18 hours. When X is Glu and Y is Lys, the mixture is preferably heated to a temperature of 215° to 225° C., most preferably about 220° C., for a time of preferably 4 to 8 hours, most preferably about 6 hours; or the mixture is heated to a temperature of 195° to 205° C., most preferably about 200° C., for a time of 18 to 30 hours, most preferably about 24 hours.

In a preferred embodiment, the crosslinked polypeptides produced by the above-described process are subjected to a mild alkaline hydrolysis. In the mild alkaline hydrolysis, the crosslinked polypeptide is exposed to an aqueous solution maintained at a pH of 9 to 13, preferably 11 to 12, at a temperature of 60° to 100° C., preferably 80° to 95° C., for a time of 0.5 to 3 hr., preferably 1 to 2 hr. The identity of the base used in the mild alkaline hydrolysis is not critical, as long as it is capable of forming aqueous solutions having the desired pH. Examples of suitable bases include sodium hydroxide and potassium hydroxide. It is preferred that the base not be ammonium hydroxide or any nucleophilic amine.

While not intending to limit the scope of the present invention, a possible explanation for the improvement afforded by the mild alkaline hydrolysis is that this hydrolysis acts to open imide rings formed between carboxyl groups and secondary amines of the polymer. The imide ring is formed during the thermal treatment. The proposed opening of the imide rings by the mild alkaline hydrolysis is shown schematically below.

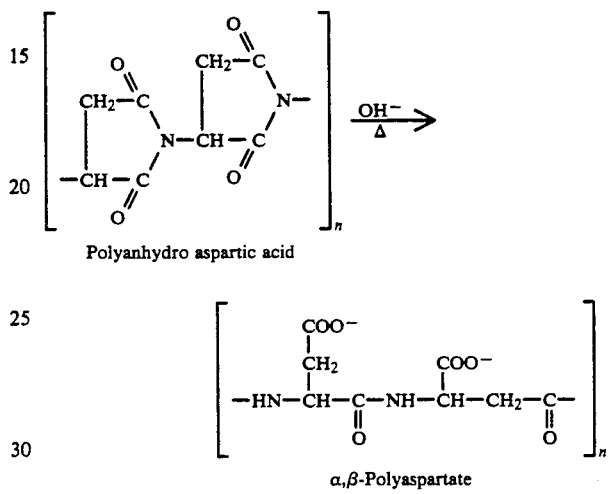

Polyanhydro aspartic acid

α,β-Polyaspartate

Upon opening of the rings, some negatively charged carboxyl groups are exposed that impart surprisingly enhanced superabsorptivity to the polyamino acids. Thus, it has been found that the superabsorbency of the present polypeptides may be improved by two to three fold by the mild alkaline hydrolysis. The polypeptides which have been prepared by the process including the mild alkaline hydrolysis have absorbencies in terms of gel volume of at least 5, preferably at least 10, as measured by the blue dextran assay described below.

It is particularly preferred to utilize the mild alkaline hydrolysis step in the production of superabsorbent polypeptides in which either X contains aspartic acid or glutamic acid or Y contains lysine.

Other features of the invention will become apparent in the course of the following descriptions of exemplary embodiments which are given for illustration of the invention and are not intended to be limiting thereof.

EXAMPLES

Method of Synthesis

For example, a mixture of polyaspartic acid, free aspartate and lysine-HCl was placed in an Erlenmeyer flask. The reaction vessel was partially submerged in cooking oil heated to 220° C. (±2° C.). A stream of nitrogen was continuously purged into the reaction vessel to eliminate $O_2$ and the possibility of charring. The reaction was allowed to continue for up to 24 hours, producing an insoluble product. This was washed by suspension in distilled water for up to 24 hours, followed by filtration and 3 washes, 300 ml each with distilled water. The final product was then lyophilized for evaluation and storage.

Methods

For some polypeptides a starting backbone of thermal polyaspartate is required to provide sufficient size of the product to render it insoluble. The polyaspartate backbone was prepared as follows;

L-aspartic acid (500 g) was placed in a Pyrex baking dish and heated at 240° C. in a muffle oven for up to 8 hours, preferably 6 hours. This resulted in nearly 100% of the aspartic acid being polymerized and no further purification was necessary. Polyanhydroaspartic acid molecules with an average molecular weight of 6000 daltons (determined by gel permeation, Sikes and Wheeler, "Control of $CaCO_3$ Crystallization by Polyanionic-hydrophobic polypeptides," in: Chemical Aspects of Regulation of Mineralization, C. S. Sikes and A. P. Wheeler, eds., Univ. of South Alabama Publication Services, Mobile, AL (1988)) were produced.

was purged through the reaction vessel to remove $O_2$ and prevent charring. Both soluble and insoluble materials resulted. The insoluble product was suspended in distilled water for 12 to 24 hours, filter washed three times (300 ml each) with distilled water and lyophilized.

Measurements of Absorbency

Fluid absorption by the polymers was measured by putting a given weight of polymer in a preweighed test tube, exposing the polymer to excess liquid for 1 hour to allow for absorption and swelling and then centrifugation at $1300 \times g$ for 15 min. The excess fluid was pipetted off, and the test tube and polymer were weighed. The absorption of fluid is given as the mass of fluid absorbed per gram of polymer. The test was performed using pure water and aqueous 1 wt. % NaCl at neutral pH. Results from use of this technique are shown in Table 1.

TABLE 1

Summary of Absorbent Peptides. Absorption of water and saline is given as the ratio of the weight of water absorbed to the weight of the dry polypeptide. D = aspartic acid, K = lysine, E = glutamic acid, NA = not applicable.

| Reactants | Temperature of Synthesis | Heating Time, Nature of the Product | Amino Acid Analysis | Absorption ($H_2O$/NaCl) |
|---|---|---|---|---|
| PolyAsp:Asp:Lys (4:2:1) | 220° C. | 6 hr, insoluble | 80.4% D/19.6% K | 50.0/31.3 |
| | | 12 hr, insoluble | 81.4% D/18.6% K | 83.9/48.3 |
| | | 15 hr, insoluble | 81.4% D/18.6% K | 81.5/45.0 |
| | | 18 hr, insoluble | 80.8% D/19.2% K | 89.9/46.7 |
| | | 24 hr, insoluble | 79.1% D/20.9% K | 58.3/27.8 |
| Glu:Lys (1:3) | 200° C. | 6 hr, (soluble) | 25.8% E/74.2% K | NA |
| | | 11 hr, (soluble) | 25.0% E/75.0% K | NA |
| | | 24 hr, (soluble) | 23.3% E/76.7% K | NA |
| | | 24 hr, insoluble | 33.1% E/66.9% K | 81.8/35.7 |
| Glu:Lys (1:3) | 220° C. | 6 hr, (soluble) | 21.7% E/78.3% K | NA |
| | | 6 hr, insoluble | 23.7% E/76.3% K | 80.0/47.8 |
| | | 24 hr, (soluble) | 17.4% E/82.6% K | NA |
| | | 24 hr, insoluble | 18.8% E/81.2% K | 50.0/32.0 |

EXAMPLE 1

Polyanhydroaspartic acid (e.g., 1.2313 g, 0.1 mole) was hydrolyzed to polyaspartic acid by aqueous suspension at pH 10, heated to 60° C. for 1 hour and then neutralized with 10N HCl. Small amounts of 10N NaOH were added during the hour to maintain the pH at 10. This solution of polyaspartic acid was placed in a 150 ml Erlenmeyer flask. L-aspartic acid (e.g., 0.8318 g, 0.05 mole) and lysine-HCl (e.g., 0.5706 g, 0.025 mole) were added. The molar ratio of amino acids for the reaction was preferably 4:2:1, polyaspartate: aspartate: lysine-HCl. The reaction vessel was partially submerged in cooking oil heated to 220° C. ($\pm 2°$ C.) for up to 24 hours, most preferably 18 hours. Nitrogen was purged through the reaction vessel to remove $O_2$ and prevent charring. The product was almost entirely insoluble and was suspended in distilled water for 12 to 24 hours, filter washed three times (300 ml each) with distilled water and lyophilized. Amino acid analysis was performed using the PICO-TAG analysis system (Waters, Millipore).

EXAMPLE 2

L-glutamic acid (e.g., 0.7355 g, 0.01 mole) and lysine-HCl (e.g., 2.739 g, 0.03 mole) were mixed together as dry powders and placed in a 150 ml Erlenmeyer flask. The preferred molar ratio of glu to lys-HCl was 1:3. The reaction vessel was partially submerged in an oil bath at 220° C. ($\pm 2°$ C.) for 24 hours. The glutamic acid melted providing a solvent for the reaction. Nitrogen

Measurement of Extractable Polymer Material

Polymer (100 mg) was placed in a 20 ml test tube. Excess fluid was added to allow for absorption and gelling of the polymer. Samples of fluid were taken at various times over a 24 hour period. These samples were analyzed for extractable polymer material by amino acid analysis techniques. Samples were hydrolyzed in 6N HCl for 1 hour at 150° C. in order to break all peptide bonds and yield free amino acids. These free amino acids were derivatized and analyzed by the Pico-Tag system (Waters, Millipore). The results are given by Table 2.

TABLE 2

Measurement of Extractable Polymer Materials. Extractable polymer material is given as picomoles of hydrolyzable free amino acids present in the fluid after exposure of the polymer for various lengths of time (mean values $\pm$ standard deviations, n = 3)

| Time (hrs) | Extractables Polyasp:asp:lys 4:2:1 |
|---|---|
| 0.5 | 16.0 ± 10.0 |
| 1.0 | 10.0 ± 2.9 |
| 1.5 | 11.0 ± 1.0 |
| 2.0 | 20.3 ± 1.9 |
| 2.5 | 62.0 ± 8.5 |
| 3.0 | 112.3 ± 11.6 |
| 3.5 | 107.3 ± 14.8 |
| 4.0 | 125.0 ± 30.6 |
| 4.5 | 104.7 ± 17.4 |
| 5.0 | 119.5 ± 13.5 |
| 5.5 | 149.0 ± 30.0 |

TABLE 2-continued

Measurement of Extractable Polymer Materials.
Extractable polymer material is given as picomoles of
hydrolyzable free amino acids present in the fluid after
exposure of the polymer for various lengths of time
(mean values ± standard deviations, n = 3)

| Time (hrs) | Extractables Polyasp:asp:lys 4:2:1 |
|---|---|
| 6.0 | 155.3 ± 12.2 |
| 7.0 | 155.0 ± 23.2 |
| 8.0 | 160.7 ± 31.5 |
| 24.0 | 384.0 ± 10.7 |

EXAMPLE 3

L-aspartic acid was thermally polymerized for 6 h at 240° C. in a Pyrex dish, producing polyanhydroaspartic acid. This was hydrolyzed in an aqueous solution at a pH of 10 and a temperature of 60° C., for 1 hour, then neutralized to pH 7 to 8 with 10N HCl, to yield polyaspartate. L-aspartic acid and L-lysine-HCL were added to this solution (up to 30% by weight polyaspartate) in a 1 liter Erlenmeyer flask. The amounts of each were 25 g of polyanhydroaspartic acid, 17.15 g of L-aspartic acid, and 11.75 g of L-lysine hydrochloride. This is a molar ratio on a residue basis of 2:1:1.

The flask was heated at 220° C. using an oil bath for 14 hours to crosslink the polyaspartate chains with lysine residues. The insoluble product was suspended in distilled water overnight, filter-washed with distilled water three times (300 ml each), and lyophilized. This produced the non-base-hydrolyzed superabsorbent.

This product was then subjected to a mild alkaline hydrolysis maintained at a pH of 10 and a temperature of 80° C., for 1 hour by additions of small amounts of 10N NaOH. Alternatively, the hydrolysis conditions were pH 12, 95° C., 2 hours. The material was then filter-washed and lyophilized, producing the hydrolyzed, improved superabsorbent.

It is not necessary to filter wash and lyophilize the product after thermal crosslinking with lysine unless the non-base-hydrolyzed material is the object of the synthesis. In cases that the base-hydrolyzed material is the objective, it is recommended to proceed directly to the base hydrolysis step after thermal crosslinking of the polyaspartate chains.

Assessment of Water Absorbency of the Polyamino Acid Superabsorbent

Gel Volume Determination

The above-described assay simply involved weighing the superabsorbent before and after absorbing water. For the non-base-hydrolyzed polyamino acid materials, this gave water absorption values for pure water in the range of 50 to 90 fold the weight of the dry polymer. Absorption values by this method for a 1 wt. % NaCl solution ranged between 30 and 50 fold.

For comparison of the mild-alkaline treated polypeptides with the non-base-hydrolyzed polypeptides the method of Brandt et al. (1988, U.S. Pat. No. Re. 32,649) was adopted.

Blue Dextran Assay for Water Absorbency

This method relies upon the exclusion of blue dextran (BD, MW~2 million d) from superabsorbent materials during the absorption of water. The extent to which the excluded (nonabsorbed) water becomes enriched in blue dextran in the presence of a superabsorbent is an indication of the amount of absorbed water. The blue dextran is assessed spectrophotometrically at 617 nm.

A typical assay involved weighing 0.1 to 0.15 g of material into each of two 50 ml beakers. To each were added 20 ml of synthetic urine (6.0 g NaCl, 0.18 g $CaCl_2.2H_2O$, 0.36 g $MgCl_2.6H_2O$, 1.5 ml of 1 wt. % aqueous Triton-X, 600 ml water) and 20 ml of a blue dextran stock (0.03 wt. % blue dextran (Sigma Chemical) in synthetic urine). The slurry in the beakers was subjected to gentle magnetic stirring for 1 hour. Next, the slurry was allowed to settle, the supernatant was collected and centrifuged for 15 minutes at 850×g. The absorbance (abs) of the centrifuged supernatant was then read at 617 nm, using the synthetic urine as reference. The gel volume was determined by the equation given below:

$$\text{Gel volume} = \frac{\text{g of BD solution}}{\text{g of superabsorbent}} \times \left[1 - \frac{\text{Abs BD solution}}{\text{Abs BD Supernat} - \text{Abs Synthetic Urine Supernat}}\right]$$

Assessment of the Charge Density of the Polyamino Acid Superabsorbent

As discussed above, base hydrolysis treatment is thought to improve the performance of the superabsorbent by converting uncharged imide residues to anionic, carboxylated residues of aspartate. To test this, the number of titratable carboxyl groups was measured for the material before and after base hydrolysis. The titrations were performed using 1N NaOH or 1N HCl, depending on the pH direction of the titration. The number of titratable groups per mg of material was calculated from the volume of HCl or NaOH required to titrate the range between pH 9.5 and 3.0. Calibration curves were made using aspartate and acrylate monomers.

The results of the dextran blue gel volume assay and titration experiments are shown below in Table 3.

TABLE 3

Improved Performance of Polyamino Acid
Superabsorbents following Mild Alkaline Hydrolysis
(mean values ± standard deviations)

| Material[1] | Dextran Blue Gel Volume (n = 3) | Titratable Groups μmoles COO−/ mg (n = 3) |
|---|---|---|
| Non-base hydrolyzed; PolyAsp-Asp-Lys; 4:2:1, 220° C., 14 h | 6.20 ± 0.09 | 4.05 ± 0.058 |
| Base hydrolyzed; pH 10, 1 h, 80° C.; PolyAsp-Asp-Lys; 4:2:1, 220° C., 14 h | 10.5 ± 0.34 | 5.68 ± 0.18 |
| Base hydrolyzed; pH 12, 2 h, 95° C.; PolyAsp-Asp-Lys; 4:2:1, 220° C., 14 h | 16.4 ± 0.54 | 6.08 ± 0.20 |

All 3 materials were composed of 82% Asp, 18% Lys as determined by PICO-TAG amino acid analysis (Waters).

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A substantially water-insoluble, crosslinked polypeptide, consisting essentially of 50 to 81.2 mole % of lysine and 18.8 to 50 mole % of glutamic acid, wherein said polypeptide has a gel volume of at least 5 as determined by the blue dextran assay.

2. The polypeptide of claim 1, consisting essentially of 18.8 to 33.1 mole % of glutamic acid and 66.9 to 81.2 mole % of lysine.

3. A substantially water-insoluble, crosslinked polypeptide, consisting essentially of 75 to 85 mole % of aspartic acid and 15 to 25 mole % of lysine, wherein said polypeptide has a gel volume of at least 5 as determined by the blue dextran assay, and wherein said polypeptide comprises at least one polyaspartic acid block having a molecular weight of about 6000 daltons.

* * * * *